United States Patent [19]

Balkovec

[11] Patent Number: 5,386,010

[45] Date of Patent: Jan. 31, 1995

[54] LIPOPEPTIDE COMPOUNDS

[75] Inventor: James M. Balkovec, N. Plainfield, N.J.

[73] Assignee: Merck & Co., Inc., Rahway, N.J.

[21] Appl. No.: 901,720

[22] Filed: Jun. 15, 1992

Related U.S. Application Data

[63] Continuation-in-part of Ser. No. 495,878, Mar. 19, 1990, abandoned.

[51] Int. Cl.$^6$ .................. A61K 37/02; C07K 5/12; C07K 7/06
[52] U.S. Cl. .................................................... 530/317
[58] Field of Search ........................... 514/11; 530/317

[56] References Cited

U.S. PATENT DOCUMENTS

| | | | |
|---|---|---|---|
| 4,287,120 | 9/1981 | Abbott et al. | 530/317 |
| 4,288,549 | 9/1981 | Boeck et al. | |
| 4,293,489 | 10/1981 | Debono | |
| 4,320,053 | 3/1982 | Abbott et al. | 530/317 |
| 4,322,338 | 3/1982 | Abbott et al. | |
| 5,159,059 | 6/1992 | Balkovec et al. | 530/317 |
| 5,306,708 | 4/1994 | Schwartz et al. | 530/317 |

FOREIGN PATENT DOCUMENTS

WO82/00587 3/1982 WIPO .

OTHER PUBLICATIONS

Satoi et al, J. Antibiotics 30, 303(1977).
Traber et al, H. Chim. Acta 62, 1252(1979).
Roy et al, J. Antibiotics 40, 275(1987).
Debono et al, J. Antibiotics 42, 389(1989).

*Primary Examiner*—Robert J. Hill, Jr.
*Assistant Examiner*—S. G. Marshall
*Attorney, Agent, or Firm*—Elliott Korsen; Mark R. Daniel; Joseph F. DiPrima

[57] ABSTRACT

Antifungal and antiparasital lipopeptide compounds stable in aqueous media are described. Stability in aqueous media render lipopeptides more useful for compositions for therapeutic applications.

15 Claims, No Drawings

LIPOPEITIDE COMPOUNDS

This is a continuation-in-part of copending application Ser. No. 07/495,878, filed Mar. 19, 1990, now abandoned.

The present invention is directed to a compound having the formula (I) (Seq. ID Nos. 1 and 2):

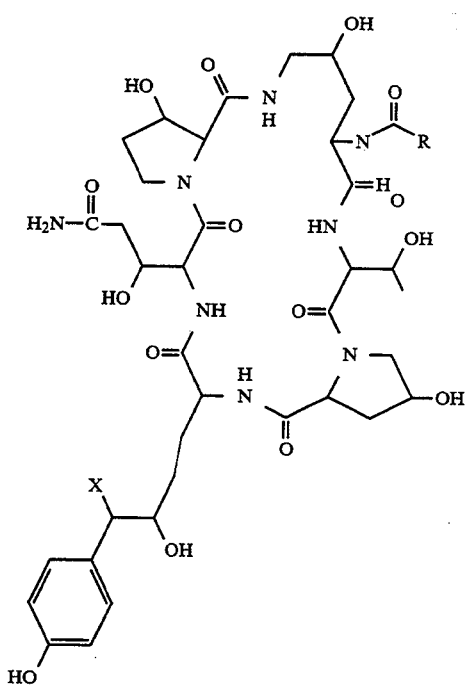

In this and succeeding formulas
X is hydrogen or hydroxyl, and
R is
a) a straight or branched chain alkyl from 5 to 23 carbon atoms;
b) a straight or branched chain alkenyl from 5 to 23 carbon atoms;
c) aryl and substituted aryl where the aryl is phenyl or naphthyl but is preferably phenyl and substituted phenyl wherein the substituent is selected from $C_1$ to $C_{10}$ alkyl, $C_1$ to $C_{10}$ alkoxy, $C_1$ to $C_{10}$ alkylamino or $C_1$ to $C_{10}$ thioalkoxy; and
d) heteroaryl and substituted heteroaryl wherein the heteroaryl is, preferably pyrryl, thiophenyl, furyl, indolyl, benzothiophenyl, benzofuryl, imidazolyl, benzimidazolyl or pyridinyl, and optionally substituted with $C_1$ to $C_{10}$ alkyl, alkoxy or thioalkoxy.

When X is H, the compound may be designated Compound IA as that having Sequence ID No. 1, having the amino acid sequence of 4-hydroxyornithine—threonine—4-hydroxyproline—3-hydroxyhomotyrosine—3-hydroxyglutamine—3-hydroxyproline and represented by Xaa-Thr-Xaa-Xaa-Xaa-Xaa. When X is OH, the compound may be designated Compound IB and as that having Sequence ID No. 2, having the amino acid sequence of 4-hydroxyornithine—threonine—4-hydroxyproline—3,4-dihydroxyhomotyrosine—3-hydroxyglutamine—3-hydroxyproline and represented by Xaa-Thr-Xaa-Xaa-Xaa-Xaa.

Represented substituents may be detailed as follows:

Representative alkyls are normal and branched heptadecyl, nonyl, nonadecyl, heptyl, tridecyl, pentadecyl and the like.

Representative alkenyls are 8,11-heptadecadienyl, 2-pentenyl, 4-heptenyl, 7-pentadecenyl, 8-heptadecenyl, 10-heptadecenyl and the like.

Representative phenyl and substituted phenyl are phenyl, tolyl, xylyl, 2-ethylphenyl, 4-ethylphenyl, 4-isopropylphenyl, 4-isooctylphenyl, 4-tert-butylphenyl, 4-decylphenyl, 3-ethoxyphenyl, 4-isopropoxyphenyl, 4-(n-nonyloxy)phenyl, 4-(n-octyloxy)phenyl, 4-(n-decyloxy)phenyl, 2,4-dimethoxyphenyl, 4-(t-butoxy)phenyl, 2-methylthiophenyl, 4-(n-nonylthio)phenyl, 4-(n-octylthio)phenyl, mesityl and the like.

Representative heteroaryls are 2-pyrryl, 3-pyrryl, 2-furyl, 3-furyl, 2-pyridinyl, 3-pyridinyl, 4-pyridinyl, 2-indolyl, 2-benzofuryl, 2-benzimidazolyl, 2-imidazolyl, thiophene-2-yl, and the like.

The preferred compounds are those in which R is alkyl from 9 to 17 carbon atoms and branched, and substituted phenyl or monoheteroaryl wherein the substituent is $C_4$ to $C_{10}$ alkoxy.

An especially preferred compound is that in which X is H and R is 9,11-dimethyltridecyl and (Seq. ID No. 1).

Another preferred compound is that in which in formula (I), X is OH and R is 9,11-dimethyltridecyl. (Seq. ID No. 2).

Still another preferred compound is that in which X is H or OH and R is 4-(n-octyl)oxyphenyl. (Seq. ID Nos. 1 and 2).

The products of the present invention have been found to have antifungal and antiparasital activity as hereinafter detailed. They are especially useful for the treatment of mycotic infections, such as those caused by the C. albicans, C. parapsilosis and other Candida organisms, as well as for the prevention and/or treatment of Pneumocystis carinii infections to which immune compromised patients are especially susceptible.

The compounds are related to certain other lipopeptides which have been found to be useful for the control of organisms causing mycotic infections and for eradicating cysts formed in Pneumocystis carinii infections but which break down in aqueous media and therefore have limited usefulness. The compounds of the present invention, however, have a property not known to be possessed by many other lipopeptides in being stable in aqueous media, particularly in the physiological pH range. This property renders the compound more useful in compositions suitable for intravenous injections which is one preferred method of treatment.

The compounds are white or light colored solids which are soluble in many organic solvents such as methanol, ethanol, dimethylformamide, aqueous acetonitrile, pyridine, aqueous tetrahydrofuran, acetic acid and the like.

The compounds of the present invention may be obtained by intimately admixing Compound A, obtained as subsequently described, with a reducing agent and a strong acid according to the following equation.

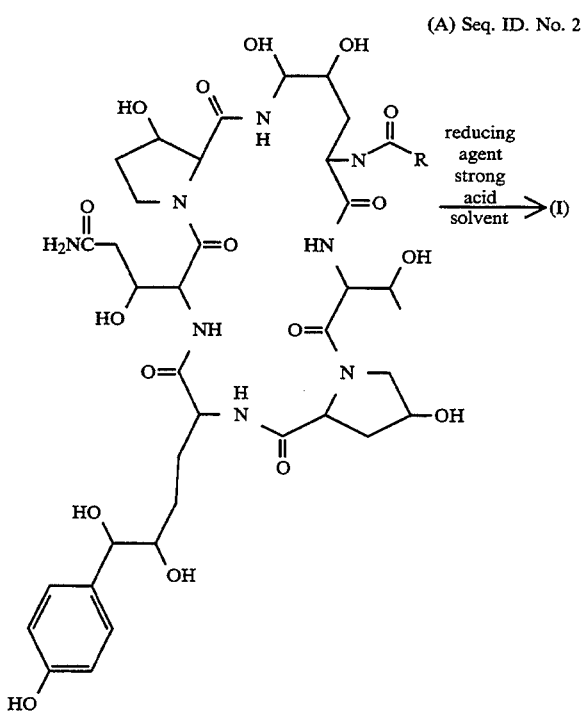

(A) Seq. ID. No. 2

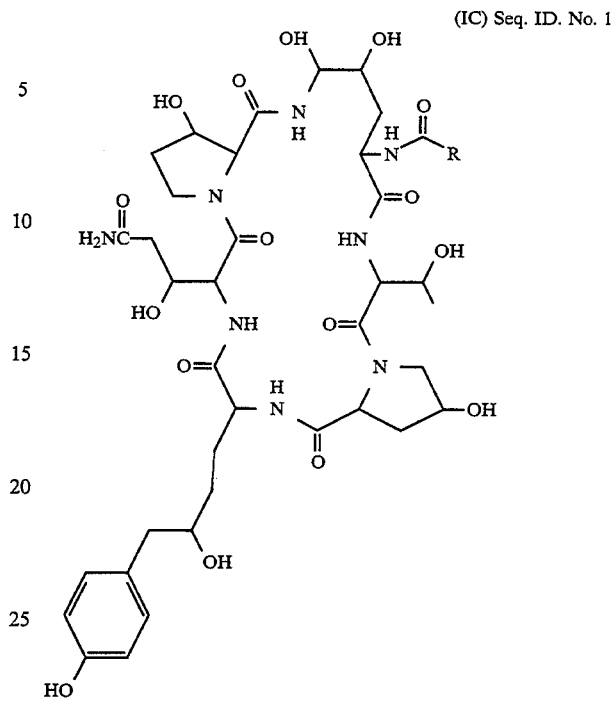

(IC) Seq. ID. No. 1

The reducing agents are selected from those which are stable in an acid environment. Representative of and particularly suitable are sodium cyanoborohydride, triethyl silicon hydride and sodium borohydride.

The reaction is carried out in the presence of a strong acid. Suitable strong acids include trifluoroacetic acid and trichloroacetic acid.

The product of the reduction may be a bis-reduced product or a mono-reduced product. When it is desired to obtain a mono-reduced product, namely, a product in which X is OH in formula (I) (Compound Ib), a solvent is employed. The solvent may be protic or non-protic. The preferred solvent for obtaining a mono-reduced product is glacial acetic acid.

When a bis-reduced product, X in formula (I) is H (Compound Ia) is desired, a separate solvent is not necessary. The strong acid serves as a suitable reaction medium.

The reaction may be summarized as follows:

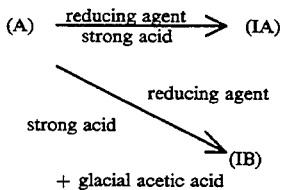

A by-product mono-reduction product (IC) is also obtained, i.e., a compound which may be represented by the following formula:

Compound Ic does not exhibit the stability in aqueous medium desired as do Compounds IA and IB, thus it is not within the scope of the present claims.

In carrying out the reaction to obtain Compound Ia, the lipopeptide is dissolved in the strong acid and to the resulting solution, is added the reducing agent while stirring at ambient temperature. Usually, the reaction takes place immediately, but stirring is continued for from about 0.5 to 4 hours to insure completion of the reaction and the formation of Compound Ia. At the end of this period, the volatiles are removed under reduced pressure to obtain a residue which is purified by reverse phase chromatography employing water/acetonitrile to obtain a purified product.

When the desired product is the mono-reduced product, essentially the same procedure is employed except that the reactant lipopeptide is first dissolved in glacial acetic acid. Thereafter, the acid is added followed by the reducing agent until the mono-reduced product is formed. This can be determined by a high performance liquid chromatography assay combined with an NMR determination. The product may be recovered and purified in the same manner as for the his-reduced product.

The compounds of the present invention are useful as antifungal agents, both against filamentous fungi and yeasts, and they are also useful as antiparasital agents, especially against protozoal parasites. As antifungal agents, the compounds are especially useful against Candida species, the causative organism of candidiasis, as hereinafter more fully illustrated, but they are also active against filamentous fungi including the causative organism for aspergillosis such as *Aspergillus flavus*, *Aspergillus fumigatus*, and *Aspergillus niger*, and other filamentous fungi such as *Cochliobolus miyabeanus* and the like. As antiparasital agents, they may be useful for the control of organisms causing amebiasis such as *Entamoeba histolytica*, or organisms causing malaria such as Plasmodium species, or other organisms such as Trypanosoma species and the like. They are especially useful in inhibiting or alleviating *Pneumocystis carinii* infections. In such use Compound I or a composition containing Compound I is administered in a therapeutically effective or inhibitory amount to subjects infected with or susceptible to being infected with *Pneumocystis carinii.*

The efficacy of the compounds of the present invention for therapeutic or anti-infective purposes against *Pneumocystic carinii* may be demonstrated in studies on immunosuppressed rats.

In a representative study, the effectiveness of Compound Ia was determined. Sprague-Dawley rats (weighing approximately 250 grams) were immunosuppressed with dexasone in the drinking water (2.0 mg/L) and maintained on a low-protein diet for five weeks to induce the development of pneumocystis pneumonia from a latent infection. Before drug treatment 2 rats were sacrificed to confirm the presence of *Pneumocystis carinii* pneumonia (PCP); both rats were found to have infections. Five rats (weighing approximately 150 grams) were injected intraperitoneally (IP) twice daily for four days with Compound Ia in 0.25 milliliter of 10% dimethylsulfoxide (DMSO) to supply drug at 0.6, 1.2 and 2.5 mg/kg of body weight. Control animals received 10% DMSO alone. All animals continued to receive dexasone in the drinking water and low protein diet during the treatment period. At the completion of the treatment, all animals were sacrificed, the lungs were removed and processed, and the extent of disease determined by microscopic analysis of stained slides. The results of the study showed that Compound Ia was effective in eliminating *P. carinii* cysts in four days with an $ED_{90}$ between 0.6 and 1.2 mg/kg.

The usefulness of the compounds as antifungal agents particularly, for the treatment of mycotic infections may be illustrated with minimum fungicidal concentration (MFC) results with Compound IA in tests against *Candida albicans, Candida tropicalis* and *Candida parapsilosis.*

The activity may be seen in a microdilution broth assay employing Yeast Nitrogen Base (Difco) with 10% dextrose (YNBD) as the medium. In carrying out the assay, Compound Ia was solubilized in 10 percent dimethyl sulfoxide (DMSO) and diluted to 2560 $\mu$g/ml. The compounds were then diluted to 256 $\mu$g/ml in YNBD. 0.15 ml of the suspension was dispensed to the top row of a 96-well plate (each well containing 0.15 ml of YNDB) resulting in a drug concentration of 128 $\mu$g/ml. Two-fold dilutions were then made from the top row to obtain final drug concentrations ranging from 128 to 0.06 $\mu$g/ml.

The yeast cultures, maintained on Sabouraud dextrose agar were transferred to YM broth (Difco) and incubated overnight at 35° C. with shaking (250 rpm). After incubation, each culture was diluted in sterile water to yield a final concentration of $1-5 \times 10^6$ colony forming units (CFU)/ml.

96-well microplates were inoculated using a MIC-2000 (Dynatech) which delivers 1.5 $\mu$l per well yielding a final inoculum per well of $1.5-7.5 \times 10^3$ cells. The microplates were incubated at 35° C. for 24 hours. The minimum inhibitory concentrations (MICs) were recorded as the lowest concentrations of drug showing no visible growth.

After recording the MIC, the plates were shaken to resuspend the cells. Thereafter, 1.5 $\mu$l samples from the wells in the 96-well microplate were transferred to a single well tray containing Sabouraud dextrose agar.

The inoculated trays were incubated 24 hours at 28° C. and then read. The MFC is defined as the lowest concentration of drug showing no growth or less than 4 colonies per spot. The results were as follows:

| Fungi Strain No. | Minimum Fungicidal Concentration ($\mu$g/ml) |
| --- | --- |
| *Candida albicans* | |
| MY 1055 | 0.25 |
| MY 1208 | 0.25 |
| MY 1028 | 0.25 |
| *Candida tropicalis* | |
| MY 1012 | 0.5 |
| *Candida parapsilosis* | |
| MY 1010 | 4.0 |

Compound I has potential as a replacement for a known antifungal agent which while effective as an antifungal agent is of limited utility for having lytic effect on red blood cells. Red blood cell lysis, a harmful and potentially fatal side reaction is shown by many compounds at concentrations approaching the therapeutic dose and this property has limited the applicability of these compounds as drugs. The compound of the present invention would require a concentration far above the therapeutic dose before red blood cell lysis could occur.

The compounds of the present invention may be effectively utilized by formulating into various novel pharmaceutical compositions including tablets, capsules, aerosols, injectible compositions and oral liquid compositions. However, the outstanding stability of the compounds in aqueous media not possessed by the precursor compounds, render the compounds of the present invention particularly adaptable to use in formulating injectible compositions or oral liquid compositions.

For both antifungal and for antipneumocystis use, Compound I may be formulated for intravenous or intraperitonal injection in a physiologically suitable injectibis carrier. The compositions may be presented in unit dosage form in ampoules or in multidose containers if necessary with an added preservative. The compositions may also take such forms as suspensions, solutions or emulsions in oily or aqueous vehicles such as 0.85 percent sodium chloride or 5 percent dextrose in water, and may contain formulating agents such as suspending, stabilizing and/or dispersing agents. Buffering agents as well as additives such as saline or glucose may be added to make the solutions isotonic. The drug also may be solubilized in alcohol/propylene glycol or polyethylene glycol for drip intravenous administration. For topical applications, the drug may be formulated in conventional creams and ointments such as white petrolatum, anhydrous lanolin, cetyl alcohol, cold cream, glyceryl-monostearate and the like. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of one of the compounds.

When the compound is to be employed for control of pneumocystis infections it is desirable to directly treat lung and bronchi. For this reason, inhalation methods are preferred. For administration by inhalation, the compounds of the present invention are conveniently delivered in the form of an aerosol spray presentation from pressurized packs of nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of Compound I in suitable propellants, such as fluorocarbons or hydrocarbons.

The following examples illustrate the invention but are not to be construed as limiting:

EXAMPLE I (Seq. ID No. 1)

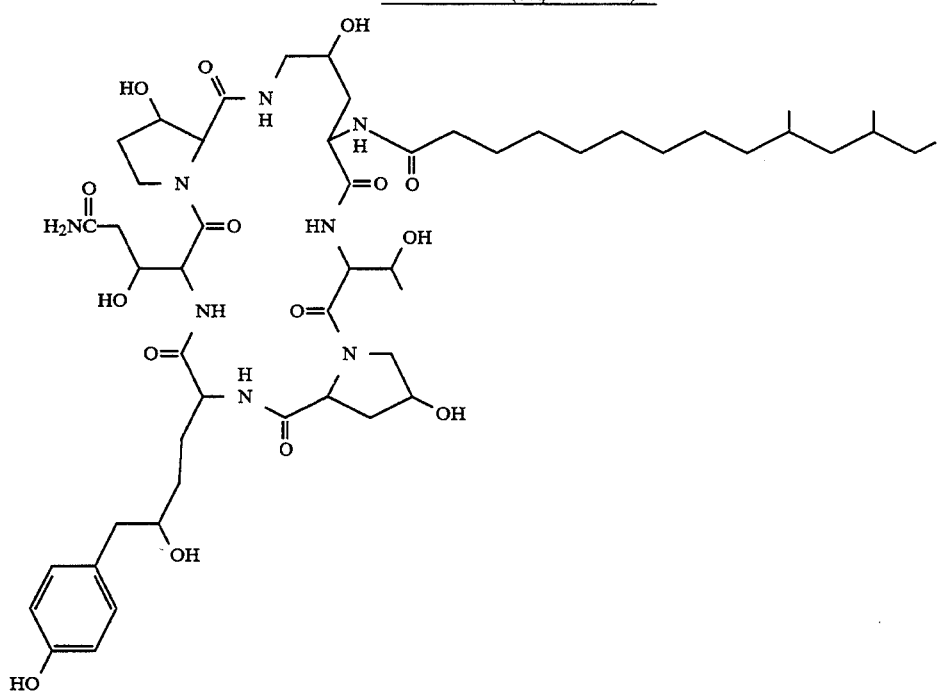

(IA-1)

A sample of Compound A-1 (R =9,11-dimethyltridecyl) of 77 percent purity (175 mg, 0.16 mmol) was dissolved in 1.0 milliliter of trifluoroacetic acid (TFA). To it was added 75 milligrams (1.2 mmol) of sodium cyanoborohydride and the solution was stirred at room temperature for 30 minutes. At the end of this period, the votaliles were removed in vacuo to produce a solid. The solid was purified by reverse phase HPLC (C8 "ZORBAX") eluting with water acetonitrile (45/55)-at a rate of 10 milliliters per minute to obtain 80 mg (98% pure, 60% yield) of Compound IA-1 (R=9,11-dimethyltridecyl) as a white solid. $^1$H-NMR (300 MHz, CD$_3$OD): $\delta$7.02 (d, J=8Hz, 2H) 2.99 (dd, J=15, 3Hz, 1H). Mass Spectra (FAB): 1033 (M+1)

EXAMPLE II

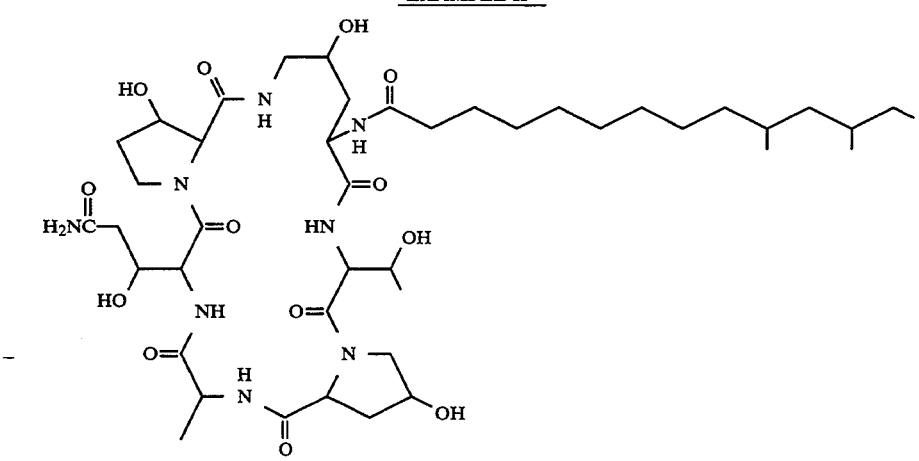

(IB 1) Seq. Id. No. 2

EXAMPLE II

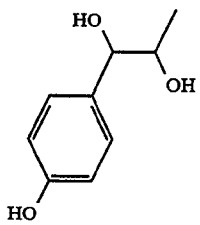

403 milligrams (0.38 mmol) of Compound A-1 (R=9,11-dimethyltridecyl) is dissolved in 10 milliliters of glacial acetic acid. To it is added 2.0 milliliters (26 mmol) of trifluoroacetic acid followed by 250 milligrams (3.99 mmol) of sodium cyanoborohydride and the resulting mixture is stirred at room temperature for several hours. The mixture is then concentrated on a rotary evaporator and purified by preparative HPLC (water/acetonitrile (50:50), 10 milliliters/minute, C8 "ZORBAX") and lyophilized to obtain the desired product having the above structure (IB-1, R=9,11-dimethyltridecyl) as a white solid. The molecular weight of the product is 1048.

EXAMPLE III

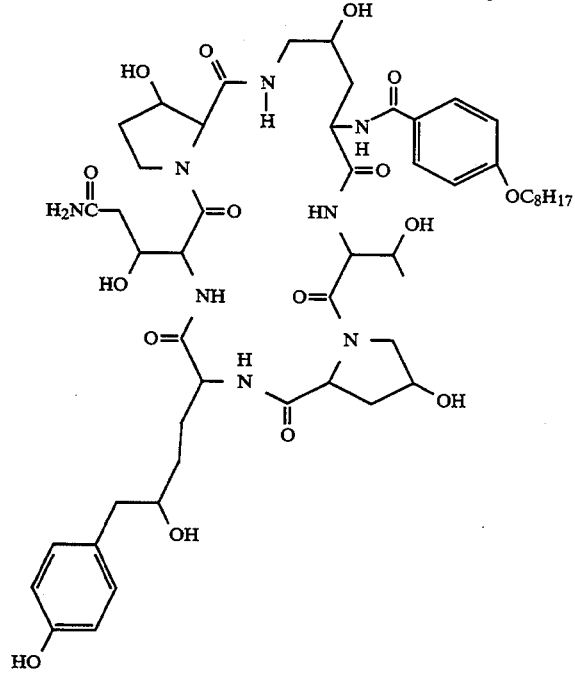

(IA-2) Seq. ID. No. 1

1.02 grams (0.963 mmol) of Compound A-2 (R=4-(n-octyl)oxyphenyl) is dissolved in 5.0 mL of trifluoroacetic acid and 0.307 gram (4.89 mmol, 5.4 eq) of sodium cyanoborohydride is added under a blanket of nitrogen. The resultant solution is stirred for 5 to 30 minutes. The TFA is removed in vacuo and the residue purified immediately by reverse phase HPLC ("ZORBAX" C8, 50% H$_2$O/50% CH$_3$CN, λ=220,277 nm). The fractions are determined by analytical HPLC and lyophilized to obtain Compound IA-2 (X is H, R is 4-(n-octyloxy)phenyl) having a molecular weight of 1027.

EXAMPLE IV

In a manner similar to that described in Example I, the following compounds may be prepared:

TABLE I

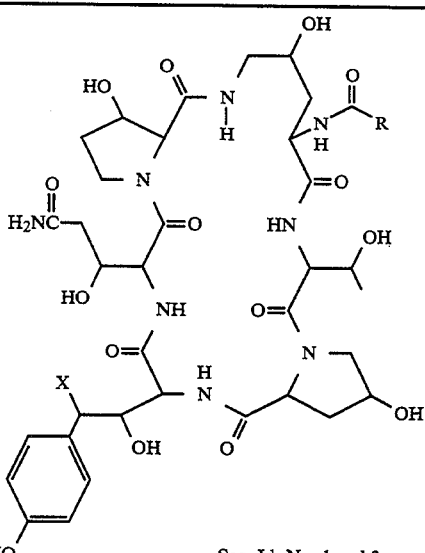

Seq. Id. No. 1 and 2

| | X | R | MW |
|---|---|---|---|
| (1) | H | —C$_{13}$H$_{27}$(n) | 1004 |
| (2) | H | —C$_{17}$H$_{25}$(n) | 1060 |
| (3) | H | —(CH$_2$)$_7$CH=CHCH$_2$CH=CH(CH$_2$)$_4$CH$_3$ | 1056 |
| (4) | H | —(CH$_2$)$_7$(CH=CHCH$_2$)$_3$CH$_3$ | 1054 |
| (5) | H | —(CH$_2$)$_7$C=C(CH$_2$)$_7$CH$_3$ | 1058 |
| (6) | H | —C$_6$H$_4$—S—C$_8$H$_{17}$ | 1042 |
| (7) | H | —C$_6$H$_4$—C$_9$H$_{19}$ | 1024 |
| (8) | H | —C$_6$H$_4$—NH—C$_4$H$_9$ | 969 |
| (9) | H | —C$_6$H$_4$—S—C$_{10}$H$_{21}$ | 1070 |
| (10) | OH | —C$_{15}$H$_{31}$(n) | 1048 |

TABLE I-continued

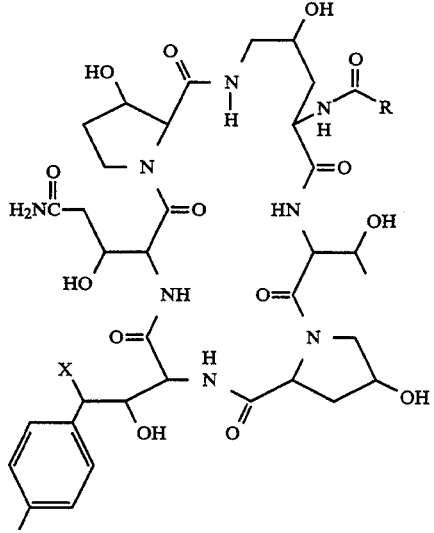

Seq. Id. No. 1 and 2

| | X | R | MW |
|---|---|---|---|
| (11) | OH | —(CH$_2$)$_{10}$—CHCH$_2$CH$_3$<br>　　　　　　　　\|<br>　　　　　　　　CH$_2$CH$_3$ | 1048 |
| (12) | OH | 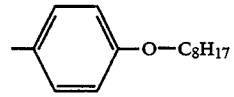 | 1042 |

EXAMPLE V 250 milliliters of an injectable preparation are prepared by conventional procedures having the following formulation:

| | |
|---|---|
| Dextrose | 12.5 grams |
| Water | 250 ml |
| Compound IA, R = 9,11-dimethyltridecyl | 400 mg |

The ingredients are blended and thereafter sterilized for use.

EXAMPLE VI

An injectable preparation is prepared by combining the following:

| | mg/ml |
|---|---|
| Compound IB, R = 9,11-dimethyltridecyl | 10 |
| Methyl cellulose | 5.0 |
| Tween 80 | 0.5 |
| Benzyl alcohol | 9.0 |
| Benzalkonium chloride | 1.0 |
| Water to 1 ml | |

Starting Material

Compound A, the starting material, when R is 9,11-dimethyltridecyl, may be obtained by cultivating *Zalerion arboricola* ATCC 20868 or ATCC 20957, in a nutrient medium providing sources of carbon, nitrogen and inorganic salts, preferably in a medium having a polyol, for 7 to 14 days with or without agitation, then recovering the desired metabolite by adding methanol and preferably partitioning into an oxygenated solvent such as ethyl acetate, thereafter removing the solvent and dissolving the residue in a solvent suitable for one or more chromatographic separations. The foregoing may be carried out by inoculating a frozen culture of *Z. arboricola* ATCC 20868 or ATCC 20957 into 54 milliliters of seed medium of the following composition: corn steep liquor, 5.0 g; tomato paste 40.0 g; oat flour 10.0 g; glucose 10.0 g; trace element mixture, 10.0 ml; all in 1000 liters of distilled water at pH 6.8. The trace element mixture contains per liter: FeSO$_4$.7H$_2$O, 1 g; MnSO$_4$.4$_2$O, 1 g; CuCl$_2$.2H$_2$O, 25 mg; CaCl$_2$, 100 mg; H$_3$BO$_3$, 56 mg; (NH$_4$)$_6$ Mo$_7$O$_{24}$.4H$_2$O, 19 mg; and ZnSO$_4$.7H$_2$O, 200 mg.

The seed flasks are incubated from 3 to 6 days at 25° C. with agitation. About 2 ml of resulting culture growth is inoculated into a production medium and incubated at 24° to 28° C. for 3 to 30 days with or without agitation. The production medium may be liquid or solid. Representative of one preferred liquid production medium is of the following composition per liter: D-mannitol, 44 grams; KH$_2$PO$_4$, 2 grams, glycine, 2 grams, peptonized milk, 15 grams, lactic acid, 2 grams; trace element mixture (composition same as above), 10 ml; soybean oil, 10 g (pre-sterilization pH of 7.0). Representative of one preferred solid production medium is of the following composition per 250 ml flask: millet, 15 g and base liquid 15 ml. The base liquid is of the following composition per liter: Ardamine PH (yeast autolysate, Yeast Products Inc., Clifton, N.J.) 33.0 g; sodium tartrate, 6.6 g; FeSO$_4$.H$_2$O, 0.66 g; monosodium glutamate, 6.6 μg; and corn oil, 6.6 ml.

It may be isolated from the fermentation mixture by filtering, then extracting the mycelium from the production medium with alcohol, preferably methanol, then partitioning the desired compound into a water-immiscible oxygenated organic solvent such as ethyl acetate, vaporizing the solvent and purifying the residue or concentrate by one or more chromatographic separations using aqueous methanol and recovering the active component with 75 percent aqueous methanol, diluting to obtain a 50:50 methanol water composition, the absorbing on "ZORBAX", eluting with 45:55 acetonitrile/water.

When in Compound A, R is other than 9,11-dimethyltridecyl, it may be prepared by deacylating Compound A in which R is 9,11-dimethyltridecyl by adding a dimethyl sulfoxide solution thereof to a resting suspension of washed *Pseudomonas acidovorans* cells (prepared as hereinafter described) in phosphate buffer at pH 6.5 and incubating for 24 hours or longer in the temperature range of 20° to 60° C. and thereafter separating from the fermentation broth by conventional methods, centrifuging to separate the cells, loading the supernatant onto a chromatographic column; eluting with methanol and concentrating to obtain eluates containing the deacylated cyclohexapepide.

The eluates are combined, diluted with water charged to a preparative HPLC system equipped with a 50 cm. Whatman Partisil 10 SCX (strong cation exchange, phenyl SO$_3$) magnum 20 column, and then eluted at 20 ml/min with 0.01M potassium phosphate (pH=6) buffer and monitored via UV at 210 nm. Cuts rich in the deacylated products were combined and the resulting mixture adsorbed and eluted from HP-20 resin with methanol to remove buffer salts and to obtain the deacylated cyclopeptide, M.W. 826.

The deacylated cyclohexapeptide then may be acylated by intimately contacting the cyclohexapeptide with an active ester

where X is an appropriate leaving group such as chloride in a solvent such as dimethylformamide and intimately contacting for 16 to 20 hours at ambient temperature, then recovering the acylated compound with the appropriate R (Compound A) by conventional organic procedures.

The properties and preparation of the organisms employed in the preparation of the starting materials are as follows:

The *Z. arboricola* ATCC 20957 (mutagenized *Z. arboricola* may be obtained by treating a spore suspension of *Z. arboricola* ATCC 20868 (obtained by first growing natural *Z. arboricola* ATCC 20868 on potato dextrose agar) in 0.3 M tris(hydroxymethyi)aminomethane (TRIS) buffer pH=7 with N-nitroso-N-methylurethane at about 300 rpm at room temperature for about 20 minutes, centrifuging and recovering the treated *Z. arboricola* and resuspending in TRIS buffer, plating on potato dextrose agar and incubating to develop colonies, thereafter isolating the colonies, transferring the separate colonies to slants of potato dextrose agar and incubating for 10 to 14 days at 25° C. to obtain cultures of mutants of *Z. arboricola*, one of which MF 5404 was deposited and registered as ATCC 20957.

The cultural and morphological characteristics of *Zalerion arboricola* ATCC 20868 or ATCC 20957 used are as follows:

Colonies on potato-dextrose agar (Difco) at 20° C. slow-growing, attaining a diameter of 8-12 mm in one week. Mature colonies (3-4 weeks on potato-dextrose agar effuse, with submerged and aerial hyphae, surface hairy, lanose, or funiculose, dull to moderately shiny, forming raised, densely compact colonies, with a substromatic texture due to dense conidia formation. Colony color pale olive-brown, olive, olive-brown, finally olive-black, Isabella Color, Sayal Brown, Tawny-olive, Saccardo's Umber, Sepia, Brownish Olive, Raw Umber, Dark Olive, Olivacsous Black (capitalized color names from R. Ridgway. 1912. Color Standards and Nomenclature, Washington, D.C.). Same colors in colony reverse. Odor, exudates, and soluble pigments absent.

Hyphae (in 3% KOH) pale yellow-brown to olive-brown, septate, branched, often with irregular lateral or terminal lobes, 1-3 um wide, thin- to slightly thick-walled, with walls smooth to slightly incrusted or verrucose. Aerial hyphae often adhering together in fascicles. Setae and hyphopodia absent.

Conidiogenous cells monoblastic, scattered to dense, integrated, terminal and intercalary, arising directly from undifferentiated hyphae, at right to slightly acute angles. Conidia originating as irregular chains, filaments, or coils, later developing as compact, irregular masses of 6-25 cells. Individual conidial cells, 3-6 $\mu$m in diameter, globose, subglobose, or slightly irregular to loved, smooth to finely verruculose, yellow-brown to olive brown.

The preparation of the deacylating enzyme is carried out by inoculating a loopful of *Pseudomonas acidovorans* ATCC 53942 into 50 milliliters of Luria Bertani medium of the following composition: per liter Bacto-Trypton, 10 g; Bacto-Yeast Extract, 5 g and sodium chloride 10 g and solidified with 2 percent agar and incubating for 24 hours with shaking to obtain a seed culture. Cells for deacylation are then grown by diluting a 50 milliliter portion of seed culture 1:500 into fresh Luria-Bertani medium and incubating at 25° C. with shaking for 16 hours. Cells are then harvested by centrifugation, washed by resuspending in 1 percent sodium chloride and centrifuged and then resuspended in potassium phosphate buffer at pH 6.5. The suspension is employed.

The cultural and morphological characteristic of *P. acidovorans* ATCC 53942 are as follows: Gram-negative aerobic rod, approximately 0.8-1.0 $\mu$m $\times$ 3.0-4.0 $\mu$m. Growth occurs on trypticase soy agar at 25°-37° C. Colonies are opaque and convex with an entire margin and glistening surface. Colonies have a butyrous texture. No pigments are observed. Growth on MacConkey agar is also observed.

The biochemical characteristics of this strain are as follows: oxidase positive, gelatin is hydrolyzed, nitrate reduced to nitrite. Growth occurs by assimilation of the following carbon sources in the presence of ammonium sulfate: D-gluconate, caprate, adipate, and malate, D-mannitol, and phenyl acetate.

---

What is claimed is:

1. A compound having the formula: (Seq. ID Nos. 1 & 2)

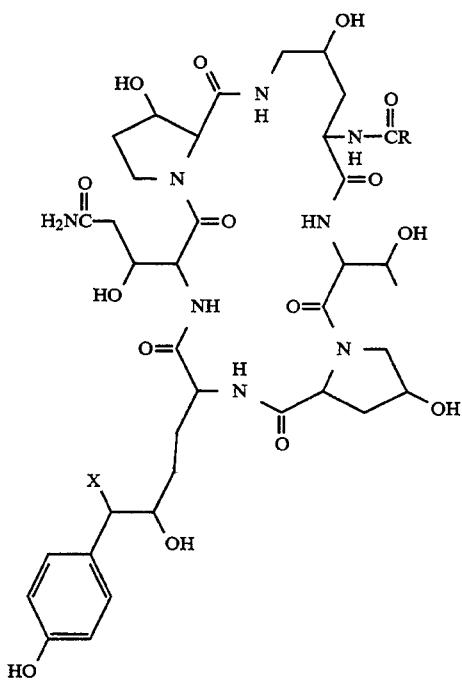

wherein
X is H or OH,
R is
  (a) a straight or branched chain alkyl from 5 to 23 carbon atoms,
  (b) a straight or branched chain alkenyl from 5 to 23 carbon atoms,
  (c) phenyl and substituted phenyl wherein the substituent is $C_1$ to $C_{10}$ alkyl, $C_1$ to $C_{10}$ alkoxy, $C_1$ to $C_{10}$ alkylamino, or $C_1$ to $C_{10}$ thioalkoxy; or
  (d) heteroaryl selected from the group consisting of pyrryl, thiophenyl, furyl, indolyl, benzothiophenyl, benzofuryl, imidazolyl, benzimidazolyl, and pyridinyl and optionally substituted with $C_1$ to $C_{10}$ alkyl, alkoxy or thioalkoxy.

2. A compound according to claim 1 wherein X is H and R is 9,11-dimethyltridecyl.

3. A compound according to claim 1 wherein X is OH and R is 9,11-dimethyltridecyl.

4. A compound according to claim 1 wherein R is phenyl or substituted phenyl wherein the substituent is $C_1$ to $C_{10}$ alkyl, $C_1$ to $C_{10}$ alkoxy $C_1$ to $C_{10}$ alkyl-amino, or $C_1$ to $C_{10}$ thioalkoxy.

5. An antibiotic composition comprising a therapeutically effective amount of the compound of claim 1 in admixture with a pharmaceutically acceptable carrier.

6. A composition according to claim 5 in which the carrier is a an aqueous liquid carrier.

7. A composition according to claim 6 which is an injectible composition.

8. A composition according to claim 6 which is a composition suitable for oral administration.

9. A composition according to claim 5 which is an aerosol composition.

10. An antibiotic composition in unit dosage form, and containing from 100 to 200 milligrams of a compound of claim 1.

11. A method for treating mycotic infections comprising administering to a patient in need of therapy, an antifungally effective amount of a compound of claim 1.

12. A method for the treatment of *Pneumocystis carinii* infections in mammals which comprises administering to mammals an anti-infective amount of the compound of claim 1.

13. A compound having the formula: (Seq. ID Nos. 1 & 2)

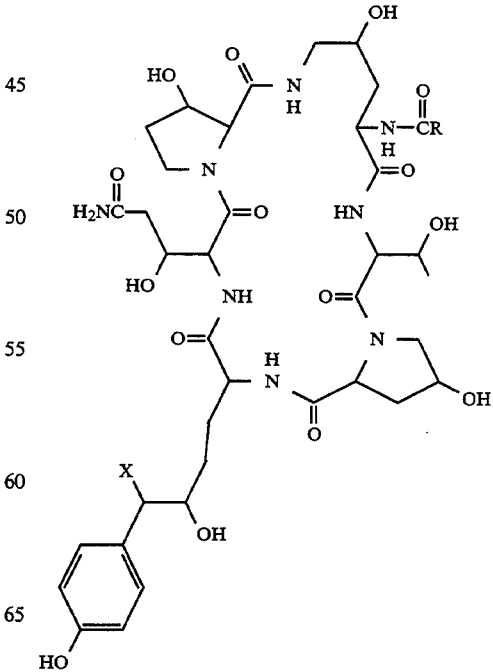

wherein
X is H or OH
R is
(1) a branched chain alkyl from 9 to 17 carbon atoms or
(2) substituted phenyl wherein the substituent is $C_4$ to $C_{10}$ alkoxy.

14. A compound according to claim 13 wherein R is 9,11-dimethyltridecyl.

15. A compound according to claim 13 wherein R is n-octyloxyphenyl.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: circular ( i i ) MOLECULE TYPE: peptide ( x i ) SEQUENCE DESCRIPTION: SEQ ID NO:1:

```
Xaa  Thr  Xaa  Xaa  Xaa  Xaa
1                 5
```

(2) INFORMATION FOR SEQ ID NO:2:

(i) SEQUENCE CHARACTERISTICS:
        (A) LENGTH: 6 amino acids
        (B) TYPE: amino acid
        (C) STRANDEDNESS: single
        (D) TOPOLOGY: circular (ii) MOLECULE TYPE: peptide (xi) SEQUENCE DESCRIPTION: SEQ ID NO:2:

Xaa Thr Xaa Xaa Xaa Xaa
1               5